United States Patent
Soppimath et al.

(10) Patent No.: US 9,061,037 B2
(45) Date of Patent: *Jun. 23, 2015

(54) STABLE BORTEZOMIB FORMULATIONS

(75) Inventors: Kumaresh Soppimath, Monmouth, NJ (US); Satish Pejaver, Bridgewater, NJ (US); Kanaiyalal R. Patel, Union, NJ (US); Lakkaraju Dasaradhi, Princeton Junction, NJ (US); Rama Sodum, Princeton, NJ (US); Hari Desu, Plainsboro, NJ (US); Navneet Puri, Bridgewater, NJ (US)

(73) Assignee: Innopharma, Inc., Piscataway, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/051,102

(22) Filed: Mar. 18, 2011

(65) Prior Publication Data

US 2011/0230441 A1 Sep. 22, 2011

Related U.S. Application Data

(60) Provisional application No. 61/315,080, filed on Mar. 18, 2010.

(51) Int. Cl.
| | | |
|---|---|---|
| A61K 31/69 | (2006.01) | |
| A61K 31/4965 | (2006.01) | |
| A61K 9/00 | (2006.01) | |
| A61K 9/08 | (2006.01) | |
| A61K 47/10 | (2006.01) | |
| A61K 9/19 | (2006.01) | |

(52) U.S. Cl.
CPC ............ *A61K 31/69* (2013.01); *A61K 31/4965* (2013.01); *A61K 9/0019* (2013.01); *A61K 9/08* (2013.01); *A61K 9/19* (2013.01); *A61K 47/10* (2013.01)

(58) Field of Classification Search
CPC .............. A61K 2300/00; A61K 31/69; A61K 31/4965; A61K 31/167; A61K 47/10; A61K 9/0019; A61K 9/08; A61K 9/19
See application file for complete search history.

(56) References Cited

U.S. PATENT DOCUMENTS

| | | | |
|---|---|---|---|
| 4,525,309 A | 6/1985 | Matteson et al. | |
| 5,780,454 A | 7/1998 | Adams et al. | |
| 6,083,903 A | 7/2000 | Adams et al. | |
| 6,297,217 B1 | 10/2001 | Adams et al. | |
| 6,617,317 B1 | 9/2003 | Adams et al. | |
| 6,699,835 B2 | 3/2004 | Plamondon et al. | |
| 6,713,446 B2 | 3/2004 | Gupta | |
| 6,747,150 B2 | 6/2004 | Adams et al. | |
| 6,958,319 B2 | 10/2005 | Gupta | |
| 7,109,323 B2 | 9/2006 | Plamondon et al. | |
| 7,119,080 B2 | 10/2006 | Adams et al. | |
| 8,063,095 B2 | 11/2011 | Laurent et al. | |
| 8,263,578 B2* | 9/2012 | Soppimath et al. | 514/64 |
| 2005/0240047 A1 | 10/2005 | Pickersgill et al. | |
| 2006/0084691 A1 | 4/2006 | Piperdi | |
| 2006/0159736 A1 | 7/2006 | Zalipsky et al. | |
| 2007/0116729 A1 | 5/2007 | Palepu | |
| 2007/0197473 A1* | 8/2007 | Frankel et al. | 514/64 |
| 2008/0038316 A1 | 2/2008 | Wong et al. | |
| 2009/0062222 A1 | 3/2009 | Sherman et al. | |
| 2009/0092661 A1 | 4/2009 | Huang et al. | |
| 2009/0099132 A1 | 4/2009 | Olhava et al. | |
| 2009/0192140 A1 | 7/2009 | Laurent et al. | |
| 2009/0222080 A1 | 9/2009 | Jukema et al. | |
| 2010/0113392 A1 | 5/2010 | Badros | |
| 2010/0135984 A1 | 6/2010 | Hyde et al. | |
| 2010/0137246 A1 | 6/2010 | Hyde et al. | |
| 2010/0226597 A1 | 9/2010 | Palle et al. | |
| 2011/0178470 A1 | 7/2011 | Kocherlakota et al. | |
| 2011/0230441 A1 | 9/2011 | Soppimath et al. | |
| 2012/0035133 A1 | 2/2012 | Bricout et al. | |

FOREIGN PATENT DOCUMENTS

| | | |
|---|---|---|
| CA | 2583520 A1 | 10/2006 |
| EP | 2238973 A1 | 10/2010 |
| JP | 2003-508436 A | 3/2003 |
| JP | 2004-517931 A | 6/2004 |
| JP | 2004-517932 A | 6/2004 |
| JP | 2007-513084 A | 5/2007 |
| KR | 10-2008-0067705 A | 7/2008 |
| WO | 2006-134864 A1 | 12/2006 |
| WO | 2008/057456 A2 | 5/2008 |
| WO | 2008/075376 | 6/2008 |
| WO | 2009/102707 | 8/2009 |
| WO | 2010/039762 | 4/2010 |
| WO | 2010/089768 | 8/2010 |
| WO | WO 2010/114982 A2 * | 10/2010 |

OTHER PUBLICATIONS

U.S. Appl. No. 13/592,235, filed Aug. 2012, Soppimath et al.*
U.S. Appl. No. 13/592,228, filed Aug. 2012, Soppimath et al.*
Vanderloo, J.P. et al., "Stability of unused reconstituted bortezomib in original manufacturer vials", Journal of Oncological Pharmaceutical Practice, Oct. 6, 2010.
Andre, P. et al., "Stability of bortezomib 1-mg/mL solution in plastic syringe and glass vial", Ann Pharmacother, Sep. 2005, 39(9), 1462-1469.
Hsieh F.Y. et al., "Elucidation of potential bortezomib response markers in multiple myeloma patients", Journal of Pharmaceutical and Biomedical Analysis, vol. 49, pp. 115-122, 2009.
Pekol, T. et al., "Human Metabolism of the Proteasome Inhibitor Bortezomib: Identification of Circulating Metabolites", The American Society for Pharmacology and Experimental Therapeutics, vol. 33, No. 6, 2005.
Stella, V.J. et al., "Prodrug strategies to overcome poor water solubility", Advanced Drug Delivery Reviews, vol. 59, pp. 677-694, 2007.

(Continued)

*Primary Examiner* — Kara R McMillian
(74) *Attorney, Agent, or Firm* — Fish & Tsang, LLP

(57) ABSTRACT

Multi-dose formulations for bortezomib are presented in which bortezomib has significantly improved stability. Especially preferred formulations include those in which bortezomib is in a liquid form suitable for injection, wherein the solvent system predominantly comprises propylene glycol. In other preferred aspects, bortezomib is present as a Lewis donor-acceptor complex with a hetero-bifunctional Lewis base.

12 Claims, No Drawings

(56) References Cited

OTHER PUBLICATIONS

Wu, S. et al., "Degradation Pathways of a Peptide Boronc Acid Derivative, 2-Pyz-(C))-Phe-Leu-B(OH)2", Department of Pharmaceutical Chemistry, the University of Kansas, 2000.

Bolognese, A. et al.; An NMR Study of the Bortezomib Degradation under Clinical Use Conditions; Advances in Hematology; vol. 2009, Article ID 704928, 5 pages; Hindawi Publishing Corporation.

Baker, S.J., et al., "Therapeutic Potential of Boron-Containing Compounds," Future Med. Chem. (2009) 1(7), 1275-1288.

ISA/KR, International Search Report and Written Opinion, International Application No. PCT/US2011/029003, Dec. 23, 2011, 9 pages.

EPO, Extended European Search Report (EESR), EPO Application No. 11757060.6, Apr. 2, 2014, 12 pages.

EPO, Extended European Search Report (EESR), EPO Application No. 12183276.0, May 10, 2013, 4 pages.

\* cited by examiner

STABLE BORTEZOMIB FORMULATIONS

This application claims the benefit of priority to U.S. provisional application with the Ser. No. 61/315,080, which was filed Mar. 18, 2010.

FIELD OF THE INVENTION

The field of the invention is bortezomib formulations with improved stability.

BACKGROUND

Bortezomib ((N-(2-pyrazine) carbonyl-L-phenylalanine-L-leucine boronic acid); sold as Velcade™, Millennium Pharmaceuticals) is a 26S proteasome inhibitor that is approved for use in treating various neoplastic diseases, and especially treatment of relapsed multiple myeloma and mantle cell lymphoma. It is believed that the boron atom in bortezomib binds to the catalytic site of the proteasome, ultimately leading to proteasome inhibition and reduced degradation of pro-apoptotic factors, which in turn triggers apoptosis in treated cells. Bortezomib and related compounds are described in U.S. Pat. Nos. 5,780,454, 6,083,903, 6,297,217, 6,617,317, 6,713,446, 6,747,150, 6,958,319, 7,119,080. These and all other extrinsic materials discussed herein are incorporated by reference in their entirety. Where a definition or use of a term in an incorporated reference is inconsistent or contrary to the definition of that term provided herein, the definition of that term provided herein applies and the definition of that term in the reference does not apply.

Unfortunately, many aminoalkylboronic acids (including bortezomib) will undergo a spontaneous 1,3-rearrangement to give the homologous amines, owing to the instability of free α-amino groups. These compounds yield boric acids and alcohols by degradation and undergo oxidative reactions that easily destroy the C—B bond which is longer and weaker than the corresponding C—C bond (see e.g., Adele Bolognese, Anna Esposito, Michele Manfra, Lucio Catalano, Fara Petruzziello, Maria Carmen Martorelli, Raffaella Pagliuca, Vittoria Mazzarelli, Maria Ottiero, Melania Scalfaro, and Bruno Rotoli. Advances in Hematology, 2009 (2009) 1-5). Such instability is borne out in stress testing and accelerated stability studies of bortezomib that has established that bortezomib in aqueous solution for injection is intrinsically unstable. For example, in an ethanol:normal saline solution (2:98, pH 2.8), Bortezomib (0.5 mg/mL) degraded 20% at 25° C. in 1 month, and in propylene glycol:ethanol:water (50:10:40), the stability of the compound improved, but still degraded 20% in 8 months when stored at 25° C. Among other factors, it was speculated that the degradation of Bortezomib observed in PEG300:EtOH:H2O (40:10:50) solvent might be due to the presence of peroxides, as PEG300 is known to undergo auto-oxidation with concomitant peroxide generation. (Journal of Pharmaceutical Sciences, 89, 2000 758-765).

In other studies, bortezomib was reported to be susceptible to oxidative degradation under a number of experimental conditions, and that the oxidation of alkyl boranes (which yields the ester of boric acid) can also be due to reaction with alkyl peracids, alkyl peroxides, or oxygen radical species. (Brown H C. 1972. Boranes in organic chemistry. Ithaca, N.Y.: Cornell University Press.) The initial oxidation can be attributed to peroxides or molecular oxygen and its radicals and as light, metal ions, and alkaline conditions normally facilitate oxidation. These conditions are therefore not considered favorable to the stability of bortezomib or any other alkyl boronic acid derivative. (Hussain M A, Knabb R, Aungust B J, Kettner C. 1991. Anticoagulant activity of a peptide boronic acid thrombin inhibitor by various routes of administration in rats. Peptides 12:1153-1154).

Formation of boronic esters from diol and polyols was reported by Kuivila et al. reporting the preparation of several esters of phenylboronic acid by reaction with sugars like mannitol and sorbitol, and 1,2-diols like catechol and pinacal. (J. Org. Chem. 1954, 8, 780-783), and reversible formation of boronic ester by the interaction of boronic acids and polyols in water was first noted by Lorand and Edwards. (J. Org. Chem. 1959, 24, 769-774). U.S. Pat. Nos. 7,119,080, 6,713, 446, 6,958,319, 6,747,150, and 6297217 disclose formation of diester of boronic acid functional group with mannitol after lyophilization. From the so formed ester, the active boronic acid is obtained upon reconstitution of the drug product in saline solution for injection. Similarly, attempts to form the ester of boronic acid with alpha-hydroxy and beta-carboxylic acids like citric acid along with bulking agents and buffers was disclosed in WO 2009/154737.

To circumvent issues with stability of bortezomib in solution, the compound can be lyophilized and reconstituted prior to injection. However, while such approach tends to solve the issues associated with bortezomib stability, unused reconstituted solution must be injected within hours or days (see e.g., Stability of unused reconstituted bortezomib in original manufacturer vials; J Oncol Pharm Pract. 2010 Oct. 6, or Stability of bortezomib 1-mg/mL solution in plastic syringe and glass vial; Ann Pharmacother. 2005 September; 39(9): 1462-6). Similarly, bortezomib esters of mannitol when reconstituted are suitable only for administration within 8 hr when stored at room temperature. Still further known approaches include isolation of specific polymorphic forms having improved stability as described in WO2008075376A1, and lyophilized forms with tromethamine as described in WO2010089768A2. Yet other formulations with selected organic solvents and other ingredients are described in WO2010039762A2. Unfortunately, all or almost all of such known compositions fail to provide significant stability for bortezomib, especially where the formulation is a liquid formulation.

Therefore, even though there are many formulations for bortezomib known in the art, all or almost all of them suffer from limited stability when bortezomib is in solution. Consequently, currently used products fail to provide flexibility of dosing, and particularly to allow multi-dose formulations with extended stability. Thus, there is still a need to provide improved alternative bortezomib formulations with greater stability.

SUMMARY OF THE INVENTION

The inventive subject matter is drawn to compositions and methods for bortezomib in which bortezomib has significantly increased stability of a prolonged period of time. In most preferred aspects, contemplated formulations are substantially non-aqueous liquid formulations and/or formulations in which bortezomib formulated with a hetero-bifunctional Lewis base donor compound to form a Lewis donor-acceptor complex.

In one preferred aspect of the inventive subject matter, a multi-dosage pharmaceutical composition is manufactured as a container for both single and multiple use that includes a liquid formulation comprising bortezomib, wherein the liquid formulation is a substantially non-aqueous solvent system suitable for injection, and wherein the solvent system comprises as a main component propylene glycol. Most preferably, the bortezomib in such formulations is present at a pharmaceutically effective concentration and in an amount sufficient for at least two independent dosages, and the solvent system is formulated to maintain degradation of the bortezomib at a level of less than 10 wt % (more typically equal or less than 8 wt %, and most typically 2-6 wt % and even lower) when the liquid formulation is stored over at least three months at ambient conditions.

It is especially preferred that the substantially non-aqueous solvent system comprises at least 50 vol %, more preferably at least 75 vol %, and most preferably 100 vol % propylene glycol. In such formulations, it is still further preferred that the substantially non-aqueous solvent system further comprises a polar solvent in an amount of equal or less than 50 vol %, more preferably equal or less than 25 vol %, and most preferably equal or less than 15 vol %. Among other choices, the polar solvent is most preferably ethanol. Alternatively, the substantially non-aqueous solvent system may include the polar solvent in an amount of equal or less than 15 vol %, and more typically equal or less than 10 vol %. In such case, the polar solvent is preferably water.

In another preferred aspect of the inventive subject matter, a pharmaceutical composition comprises bortezomib and a hetero-bifunctional Lewis base, wherein the bortezomib and the hetero-bifunctional Lewis base together are present in form of a Lewis donor-acceptor complex, and wherein especially preferred hetero-bifunctional Lewis bases have at least two distinct donor groups (most preferably selected from —NH$_2$, —SH, COOH, and —OH). Such contemplated formulations will preferably be lyophilized or in solution.

It is generally preferred that in such formulations bortezomib and the hetero-bifunctional Lewis base are present in a ratio of 1:200, more preferably in a ratio of 5:80, and most preferably in a ratio of 20:40. Most typically, preferred hetero-bifunctional Lewis bases include amino acids (e.g., naturally occurring amino acid or an N-acetylated amino acid), peptides (e.g., naturally or synthetic dipeptides or tripeptides), and substituted polyethylene glycols. Particularly preferred substituted polyethylene glycol have a structure according to Formula I Formula I $$A\text{-}\left[\text{O}\underset{A}{\overset{A}{-}}\right]_n\text{-}A$$

wherein n is an integer between 2 and 5,000, and wherein each A is independently selected from the group consisting of hydrogen, —NH2, —SH, COOH, and —OH. Where the composition is lyophilized, it is preferred that the formulation includes a buffering agent, a lyoprotectant, a cryoprotectant, a preservative, and/or an antioxidant.

Various objects, features, aspects and advantages of the inventive subject matter will become more apparent from the following detailed description of preferred embodiments.

DETAILED DESCRIPTION

The present invention is generally directed towards to pharmaceutical compositions and methods of preparing liquid and lyophilized formulations containing therapeutically effective concentrations of bortezomib, where the formulation provides significantly improved stability for bortezomib. Where the formulation is lyophilized or concentrated above the concentration suitable for injection, contemplated compositions will be administered after reconstitution with one or more pharmaceutically acceptable diluents, optionally further containing pharmaceutically acceptable antioxidants, stabilizers, preservatives and/or co-solvents.

In certain aspects of the inventive subject matter, contemplated formulations will include bortezomib and a hetero-bifunctional Lewis base donor to so form a donor acceptor complex, while in other aspects contemplated formulations are liquid formulations and will include an at least binary non-aqueous solvent system. In still further contemplated aspects, bortezomib and/or bortezomib donor acceptor complexes may also be encapsulated in a pharmaceutically acceptable delivery or carrier system, particularly in liposomes, micelles, nanoparticles, microspheres, emulsions, and/or suspensions. Regardless of the particular form of preparation, contemplated formulations may further include stabilizing agents, buffer components, anti-oxidants, isotonicity adjusting agents and lyoprotective agents.

Most typically, contemplated pharmaceutical formulations are stable for months at ambient conditions (i.e., 25° C., 60% relative humidity) when stored in an amber vial with nitrogen head space. Most typically, contemplated formulations will be subjected to sterile filtration, and when lyophilized, can be reconstituted with intravenous diluents such as saline, dextrose, or water for injection.

For example, in one preferred aspect, contemplated pharmaceutical compositions will include a liquid formulation that includes bortezomib in a substantially non-aqueous solvent system suitable for injection, and wherein the solvent system comprises propylene glycol as a main component. The term "substantially non-aqueous solvent system" refers to a solvent system in which bortezomib is completely soluble without water and that comprises water in a total amount of equal or less than 15 vol %. Where desired an antioxidant may be included in the formulation. In another preferred example, contemplated pharmaceutical compositions will include a formulation in which bortezomib and a hetero-bifunctional Lewis base form a Lewis donor-acceptor complex. Most typically, the hetero-bifunctional Lewis base has at least two distinct donor groups (preferably selected from the group of —NH$_2$, —SH, COOH, and —OH), and the formulation is lyophilized or in solution. As used herein, the term "donor acceptor complex" refers to a non-covalent and non-ionic association with a stability that is intermediate with respect to stability of covalent and ionic bonds.

Most preferably, bortezomib and the hetero-bifunctional Lewis base are present in a ratio of 1:100 to 1:200, more typically 1:10 to 1:100, and most typically 1:1 to 1:10. Unless the context dictates the contrary, all ranges set forth herein should be interpreted as being inclusive of their endpoints, and open-ended ranges should be interpreted to include commercially practical values. Similarly, all lists of values should be considered as inclusive of intermediate values unless the context indicates the contrary.

Therefore, and viewed from another perspective, the present inventive subject matter is drawn to compositions and pharmaceutical formulations comprising bortezomib in a stable liquid dosage form or as a stable lyophilized product. In most instances, the inventors contemplate that the stable in liquid forms provide stability of bortezomib at ambient conditions for at least two, more typically six, and most typically 12 months and even longer. As further shown below (see examples, further data not shown), contemplated formulations provided significant stability to bortezomib in various solvent systems, and preferred solvent systems were formulated such that degradation of bortezomib was maintained at or below 10 wt %, more typically at or below 8 wt %, even more typically at or below 6 wt %, and most typically at or below 4 wt % and even at or below 2 wt % where the liquid formulation was stored over at least three months at ambient conditions. Similarly, where bortezomib is in lyophilized form, contemplated forms will provide stability of bortezomib at ambient conditions for at least two, more typically 6, and most typically 12 months and even longer. It should be appreciated that bortezomib may be present in contemplated pharmaceutical formulations in any suitable amount, and most preferably in an amount that is suitable for injection after reconstitution. Thus, and viewed from a different perspective, bortezomib is present in a therapeutically effective amount to treat a neoplastic (or other) condition in a human or other non-human mammal. In preferred aspects, bortezomib is present in a therapeutically effective amount to treat cancer. Typically, the Bortezomib is present in an amount of about 0.01% to about 99% w/w of the total composition.

In especially preferred aspects, the non-aqueous solvent system is a single solvent or a binary solvent system, which may optionally further include a buffer. While various alternative solvents are also deemed suitable for use herein, particularly preferred solvents and solvent systems include propylene glycol, one or more short chain alcohols ($C_1$-$C_6$), dimethyl acetamide, N-methylpyrrolidone, dimethyl sulphoxide, and glycerol. Viewed from a different perspective, suitable solvents especially include polar non-protic and protic solvents. Where the solvent system is a binary system it is preferred that the solvents are two or more of short chain alcohols (e.g., ethanol, tert-butyl alcohol), aryl alcohols (e.g., benzyl alcohol), glycols (and especially propylene glycol), dimethyl acetamide N-methylpyrrolidone, and dimethyl sulphoxide.

Unexpectedly, the inventors further discovered that certain solvents allowed formation of a stable and liquid formulation, while closely related solvents lead to rapid degradation. For example, and as can be seen further below, propylene glycol allowed formation of a stable solution of bortezomib while solutions with polyethylene glycol typically lead to rapid degradation of the bortezomib. Similarly, ethanol in relatively low concentrations (e.g., equal or less than 25 vol %, more typically equal or less than 20 vol %) afforded a stable formulation while ethanol quantities above 25 vol % led to marked degradation. It should further be appreciated that especially preferred solvents (e.g., propylene glycol, ethanol) will not lead to ester or di-ester formation, even in formulations with low (e.g., equal or less than 15 vol %) or no water content.

Likewise, it should be noted that bortezomib will not form an ester or di-ester with a (hetero-)bifunctional Lewis base donor molecule. Instead, bortezomib will form in most cases a donor acceptor complex that is intermediate in stability to an ionic bond and a covalent bond. Thus, the boronic acid moiety remains protected in solution or in lyophilized state without ester formation, leading to significantly improved stability. For example, suitable hetero-bifunctional Lewis base donors include compounds with two or more —OH, —SH, —COOH, and/or —NH2 groups, which are most typically vicinal groups or separated by no more than 4 atoms in linear dimension. For example, suitable hetero-bifunctional Lewis base donors include compounds include compounds in which the two hetero-functional groups are —OH and —SH, —OH and —NH2, —SH and —NH2, —COOH and —NH2, and —COOH and —SH.

A large variety of hetero-bifunctional Lewis base donors are known in the art and especially preferred donors include numerous amino acids (e.g., proteinogenic, essential, non-essential, chemically modified, synthetic, beta-, gamma-amino acids, etc. acids), all of which may be in D- or L-configuration. For example, contemplated amino acids include alanine, asparagine, aspartic acid, arginine, cysteine, glutamine, glycine, glutamic acid, histidine, isoleucine, lysine, leucine, phenylalanine, methionine, serine, proline, tryptophan, threonine, tyrosine and valine.

In further examples, the hetero-bifunctional Lewis base donor may also be a synthetic or natural peptide, and especially a dipeptide, a tripeptide, or an oligopeptide. Examples of peptides include carnosine, anserine, homoanserine, kyotorphin, balenine, aspartame, glorin, barettin, pseudoproline, glycylglycine, isoleucine-proline-proline (ipp), glutathione, thyrotropin-releasing hormone, melanostatin, ophthalmic acid, leupeptin, and eisenin. Oligopeptides are also deemed suitable, albeit less preferred.

In still further contemplated examples, hetero-bifunctional Lewis base donors may also be various polymers with pendant and/or terminal Lewis base donor groups. Among other preferred choices, especially suitable polymers include pharmaceutically acceptable polymers, including substituted polyethylene glycols with structure according to Formula I

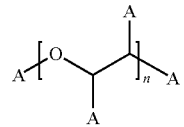

Formula I wherein n is an integer between 2 and 5,000, and wherein each A is independently selected from the group consisting of hydrogen, —NH$_2$, —SH, COOH, and —OH. In still further preferred aspects, the polymer may also comprise a carbohydrate backbone that is derivatized with two or more distinct Lewis donor groups. Of course, it should be appreciated that all polymers are especially that are pharmaceutically acceptable.

It should be further noted that the complex of the hetero-bifunctional Lewis base donor with bortezomib may be formed in numerous manners, and particularly suitable manners include heating in a solvent of choice for an appropriate period of time. Alternatively, complexes or esters can also be prepared by evaporation of solvent, salting out, or precipitation (facilitated by seeding). A further especially preferred manner is co-lyophilization of bortezomib with a hetero-bifunctional Lewis base donor, typically from an aqueous solution comprising of bortezomib and a molar excess of the hetero-bifunctional Lewis base donor. In some embodiments, the aqueous solution additionally comprises a (preferably water-miscible) co-solvent. Example of suitable co-solvents includes, but not limited to tert-butyl alcohol, methanol, ethanol, and mixtures thereof. While the molar excess of the hetero-bifunctional Lewis base donor relative to bortezomib can be in a wide range, it is generally preferred that the excess is between 1:1 to 1:200, more typically 1:100 to 1:200, even more typically 1:10 to 1:100, and most typically 1:1 to 1:10.

Depending on the particular formulation, contemplated compositions may comprise one or more bulking agent, cryoprotectant, or lyoprotectants to facilitate lyophilization. In some embodiments, the Lewis base donor molecule may also act as a bulking agent, cryoprotectant, lyoprotectants, and/or stabilizer. Further suitable lyoprotectants including amino acids, and polymers. Preferably, amino acids will be selected from lysine, alanine, glycine. Suitable polymers include various proteins (e.g., gelatin, albumin, etc.), polyethylene glycol, polyvinyl pyrrolidone, and Dextran-40. Most typically, the lyoprotectant represents less than 50% w/w of the total composition, and all concentrations above 1% w/w of the total composition are deemed effective to enhance the stability of the formulation. Thus, the lyoprotectant may be present in an amount of at least about 5% w/w, at least about 10% w/w, or at least about 20% w/w of the total composition.

The compositions contemplated herein may further include tonicity agents, and suitable tonicity agents include sodium chloride, glycerol, thioglycerol. Additionally, contemplated formulations may include further pharmaceutically acceptable excipients, and especially buffers, preservatives, and antioxidants, and any reasonable mixture thereof. However, in at least some formulations, the inventors unexpectedly discovered that formulations without antioxidants (and particularly without N-acetyl cysteine) had increased stability.

It should further be appreciated that depending on the particular ingredients, the pH of the formulation may vary. However, it is generally preferred that the pH of the formulations is suitable for injection and will typically be between 4.0 and 9.0, more typically between 5.5 and 8.0. Thus, one or more buffer systems may be employed to stabilize the pH at a desired value or range. Suitable buffers include citric acid buffer, acetic acid buffer, maleic acid buffer, phosphoric acid buffer, succinic acid buffer, and tartaric acid buffer. Most typically, the buffer strength is between 5 mM to 150 mM, however, higher and lower strengths are also deemed suitable for use herein. To still further improve the stability, the formulations may also include one or more anti-oxidants. For example, hydrophobic anti-oxidants include butylated hydroxytoluene, butylated hydroxyanisole, propyl gallate, and α-tocopherol, DL-tocopherol, α-tocopherol acetate, Tocopherol Polyethylene Glycol Succinate (Vitamin E TPGS), L-cysteine, or hydrophilic anti-oxidants, including sodium EDTA and thioglycerol. Most typically, the concentration of the anti-oxidant will be between 0.005% and 5% w/w of the total composition. Additionally, or alternatively, contemplated formulations may include a preservative (e.g., phenol, thimerosal, chlorobutanol, benzyl alcohol, m-cresol, phenoxyethanol, methylparaben and propylparaben), typically at a concentration of between 0.001% w/w and less than 5% w/w of the total composition, and most typically between 0.003% and 2.0% w/w of the total composition.

It should further be appreciated that contemplated formulations will be sterilized and all known manners of sterilization are deemed suitable for use herein, including filtration through 0.22 micron filters, heat sterilization, radiation (e.g., gamma, electron beam, microwave), and/or ethylene oxide sterilization to render the formulations sterile. Where contemplated formulations are lyophilized, they may be prepared as lyophilized cake, lyophilized powder, etc. The solutions or lyophilized forms may be diluted and/or reconstituted with standard intravenous diluents known in the art. For example, suitable intravenous diluents for use in the present invention include water, saline, dextrose 5% in water, water for injection or lactated ringer's solution.

Regardless of the particular formulation, it is especially preferred that the formulation is packaged in a container suitable for both single and multi use. Thus, especially preferred containers include an ampoule, a vial, a pre-filled syringe, and intravenous bag. Especially preferred multi-use containers will contain bortezomib in an amount suitable to allow at least two distinct uses, more typically at least five, and most typically at least ten distinct uses.

Thus, it should be appreciated that contemplated formulations will typically allow storage of the bortezomib for at least 1 week after first use, more typically at least 2-4 weeks after first use, and most typically at least 1-3 months (and even longer) after first use without significant degradation (i.e., less than 10% degradation) of the bortezomib under ambient conditions. Bortezomib may therefore be formulated for administration to human and various animals, and especially mammals. For example, formulations may be in the form of a solution for injection (e.g., injectable multi dose sterile composition), in the form of a sterile powdered composition (e.g., lyophilized cake, powder, lyophilized powder), which may be administered after dilution or reconstitution.

EXAMPLES

The following experiments are provided to exemplarily illustrate various aspects of the inventive subject matter presented herein. However, it should be apparent to those skilled in the art that many more modifications besides those already described are possible without departing from the inventive concepts herein.

Non-Aqueous Formulations (1):

Five non-aqueous formulations were prepared with various ingredients shown in Table 1. More particularly, a stock solution of D/L-Tocopherol was made by dissolving 625 mg of D/L-Tocopherol in 25 ml of ethanol, and a stock solution of butylated hydroxytoluene (BHT) and butylated hydroxyanisole (BHA) were prepared by dissolving 15 mg of each in 100 ml of ethanol, respectively. All five formulations were prepared by dissolving, 20 mg of bortezomib in 200 proof 10 ml ethanol and 100 μl of DL Tocopherol ethanolic stock, 0.2 ml of BHT and BHA stock were added accordingly as per Table 1. Samples were then stored in an amber vial with nitrogen head space and stored at various storage conditions as indicated in the tables.

TABLE 1

| Ingredients | Formulation I | Formulation II | Formulation III | Formulation IV | Formulation V |
|---|---|---|---|---|---|
| Bortezomib | 4.0 mg | 4.0 mg | 4.0 mg | 4.0 mg | 4.0 mg |
| Ethanol | 2.0 ml | 2.4 ml | 2.2 ml | 2.2 ml | 10.0 ml |
| Propylene Glycol | 8.0 ml | 7.6 ml | 7.8 ml | 7.8 ml | — |
| Dl Tocopherol % w/v | | 0.05 | 0.05 | 0.05 | |
| Butylated Hydroxy Toluene % w/v | | 0.00003 | | 0.00003 | |
| Butylated Hydroxy Anisole % w/v | | 0.00003 | | 0.00003 | |

Stability results are shown in Tables 2-4, wherein Table 2 lists results for the stability tests of bortezomib at 40° C. and 75% relative humidity, Table 3 lists results for the stability tests of bortezomib at 25° C. and 60% relative humidity, and Table 4 lists results for the stability tests of bortezomib at 4° C.

TABLE 2

| | Formulation | | | | |
|---|---|---|---|---|---|
| | I | II | III | IV | V |
| Assay | | | | | |
| 1M | 93 | 91 | 94 | 91 | 76 |
| 2M | 95 | 91 | 93 | 94 | 65 |
| 3M | 93 | 91 | 92 | 92 | 51 |

TABLE 2-continued

| | Formulation | | | | |
|---|---|---|---|---|---|
| | I | II | III | IV | V |
| Impurity I (0.72 RRT) | | | | | |
| 1M | 1.1 | 1.29 | 1.05 | 1.13 | 12 |
| 2M | 1.9 | 4.22 | 3.17 | 2.63 | 26 |
| 3M | 3.2 | 3.94 | 3.86 | 3.36 | 41 |
| Impurity III (1.12 RRT) | | | | | |
| 1M | 2.01 | 2.01 | — | 3.66 | 8.9 |
| 2M | 0.99 | 1.40 | 1.38 | 1.30 | 5.4 |
| 3M | 2.14 | 2.02 | 2.18 | 1.92 | 4.3 |
| Impurity IV (1.28 RRT) | | | | | |
| 1M | 1.15 | 0.14 | 1.24 | 1.4 | 0.38 |
| 2M | 1.18 | 2.21 | 1.88 | 1.52 | 0.07 |
| 3M | 1.25 | 1.43 | 1.29 | 1.4 | 0.12 |
| Impurity V (1.42 RRT) | | | | | |
| 1M | — | — | — | 0.08 | — |
| 2M | 0.10 | 0.23 | 0.16 | 0.16 | 0.03 |
| 3M | 0.15 | 0.19 | 0.18 | 0.17 | 0.03 |
| Impurity VI (2.15 RRT) | | | | | |
| 1M | — | — | — | — | — |
| 2M | 0.06 | 0.14 | | 0.12 | 1.79 |
| 3M | 0.17 | 0.19 | 0.19 | | 2.40 |

TABLE 3

| | Formulation | | | | |
|---|---|---|---|---|---|
| | I | II | III | IV | V |
| Assay | | | | | |
| 1M | 94.39 | 94.41 | 95.2 | 95.2 | 90.6 |
| 2M | 98.96 | 98.55 | 98.6 | 98.8 | 92.6 |
| 3M | 98.75 | 98.07 | 98.24 | 98.49 | 88.37 |
| Impurity I (0.72 RRT) | | | | | |
| 1M | 0.1 | 0.13 | 0.08 | 0.11 | 1.38 |
| 2M | 0.2 | 0.27 | 0.26 | 0.23 | 2.91 |
| 3M | 0.27 | 0.38 | 0.35 | 0.33 | 5.44 |
| Impurity III (1.12 RRT) | | | | | |
| 1M | — | — | — | — | 4.55 |
| 2M | — | — | — | — | 3.62 |
| 3M | — | — | — | — | 5.15 |
| Impurity IV (1.28 RRT) | | | | | |
| 1M | 0.73 | 0.91 | 0.8 | 0.94 | — |
| 2M | 0.62 | 1.03 | 0.9 | 0.72 | 0.06 |
| 3M | 0.77 | 1.04 | 1.21 | 1.04 | 0.07 |
| Impurity V (1.42 RRT) | | | | | |
| 1M | — | — | — | — | — |
| 2M | 0.06 | 0.08 | 0.07 | 0.07 | — |
| 3M | 0.07 | 0.09 | 0.09 | 0.08 | — |
| Impurity VI (2.15 RRT) | | | | | |
| 1M | — | — | — | — | — |
| 2M | — | — | — | — | 1.02 |
| 3M | — | — | — | — | 0.77 |

TABLE 4

| | Formulation | | | | |
|---|---|---|---|---|---|
| | I | II | III | IV | V |
| Assay | | | | | |
| 3M | 99.47 | 99.31 | 99.38 | 99.40 | 98.8 |
| Impurity I (0.72 RRT) | | | | | |
| 3M | 0.10 | 0.10 | 0.10 | 0.10 | 0.59 |
| Impurity III (1.12 RRT) | | | | | |
| 3M | — | — | — | — | — |
| Impurity IV (1.28 RRT) | | | | | |
| 3M | 0.36 | 0.48 | 0.40 | 0.39 | 0.40 |
| Impurity V (1.42 RRT) | | | | | |
| 3M | 0.06 | 0.06 | 0.06 | 0.06 | 0.11 |
| Impurity VI (2.15 RRT) | | | | | |
| 3M | | | | | 0.07 |

Non-Aqueous Formulations (2):

Five substantially non-aqueous formulations were prepared with various ingredients as shown in Table 5. The formulations were prepared as follows: Degas the water for injection (WFI) to remove the dissolved oxygen in WFI and Propylene Glycol, refined Polyethylene Glycol 300 and Acetate buffer, weigh required amount of Bortezomib and add to the compounding vessel and dissolve in PG or PEG in the compounding vessel with stirring. After complete dissolution of the drug add remaining amount of vehicle such as propylene glycol, polyethylene glycol, and buffer. In case of the formulation with N-acetyl cysteine, add and dissolve N-acetyl cysteine in buffer under nitrogen and add to the drug solution.

TABLE 5

| Ingredients | Concentration (mg/mL) | Batch Quantity |
|---|---|---|
| Formulation A | | |
| Bortezomib | 1 | 25.0 mg |
| Propylene Glycol | qs | 25 gm |
| Formulation B | | |
| Bortezomib | 1 | 25.0 mg |
| Refined PEG | qs | 25 gm |
| Formulation C | | |
| Bortezomib | 1 | 25.0 mg |
| Propylene Glycol | 45 | 12.5 gm |
| Acetate Buffer | 5 | 12.5 gm |
| Formulation D | | |
| Bortezomib | 1 | 25.0 mg |
| Propylene Glycol | 25 | 22.5 gm |
| Acetate Buffer | 25 | 2.5 gm |
| Formulation E | | |
| Bortezomib | 1 | 50.0 mg |
| Propylene Glycol | 25 | 25 gm |
| Acetate Buffer | 25 | 25 gm |
| N-Acetyl Cysteine | 5 | 0.250 gm |

Stability results are shown in Tables 6-8, wherein Table 6 lists results for the 2-week stability tests of bortezomib at certain storage conditions, Table 7 lists results for the 6-week stability tests of bortezomib at certain storage conditions, and Table 8 lists results for the 2-month stability tests of bortezomib at certain storage conditions.

TABLE 6

| Formulation | Initial | 2 Week | |
|---|---|---|---|
| Storage Condition | | 25° C./60% RH | 40° C./75% RH |
| Formulation A Bortezomib (1 mg/ml) in 100% PG | | | |
| Assay % | 100 | 100 | 99.5 |
| % Highest Impurity | ND | ND | 0.13 |
| Formulation C Bortezomib (1 mg/ml) in 50% PG and 50% Acetate Buffer | | | |
| Assay % | 99.65 | 99.86 | 99.26 |
| % Highest Impurity | ND | 0.14 | 0.62 |
| Formulation D Bortezomib (1 mg/ml) in 90% PG and 10% Acetate Buffer | | | |
| Assay % | 99.84 | 98.34 | 99.61 |
| % Highest Impurity | | 0.18 | ND |
| Formulation E Bortezomib (1 mg/ml) in 90% PG and 10% Acetate Buffer with NAC | | | |
| Assay % | 99.74 | 99.88 | 84.52 |
| % Highest Impurity | 0.16 | 0.12 | 7.11 |

TABLE 7

| Formulation | Initial | 6 Week | | |
|---|---|---|---|---|
| Storage Condition | | 0-4° C. | 25° C./60% RH | 40° C./75% RH |
| Formulation A Bortezomib (1 mg/ml) in 100% PG | | | | |
| Assay % | 100 | 100 | 99.64 | 98.25 |
| % Highest Impurity | ND | ND | 0.14 | 0.65 |
| Formulation C Bortezomib (1 mg/ml) in 50% PG and 50% Acetate Buffer | | | | |
| Assay % | 99.65 | 99.42 | 99.01 | 94.83 |
| % Highest Impurity | ND | 0.08 | 0.42 | 1.93 |
| Formulation D Bortezomib (1 mg/ml) in 90% PG and 10% Acetate Buffer | | | | |
| Assay % | 99.84 | 99.85 | 99.56 | 98.34 |
| % Highest Impurity | | ND | 0.16 | 0.51 |
| Formulation E Bortezomib (1 mg/ml) in 90% PG and 10% Acetate Buffer with NAC | | | | |
| Assay % | 99.74 | 62.36 | 91.64 | 44.21 |
| % Highest Impurity | 0.16 | 1.16 | 0.28 | 27.42 |

TABLE 8

| Formulation | Initial | 2 Month | | |
|---|---|---|---|---|
| Storage Condition | | 0-4° C. | 25° C./60% RH | 40° C./75% RH |
| Formulation A Bortezomib (1 mg/ml) in 100% PG | | | | |
| Assay % | 100 | 99.79 | 99.32 | 97.46 |
| % Highest Impurity | ND | 0.07 | 0.23 | 0.98 |
| Formulation C Bortezomib (1 mg/ml) in 50% PG and 50% Acetate Buffer | | | | |
| Assay % | 99.65 | 98.66 | 97.67 | 88.66 |
| % Highest Impurity | ND | 0.11 | 0.72 | 3.29 |
| Formulation D Bortezomib (1 mg/ml) in 90% PG and 10% Acetate Buffer | | | | |
| Assay % | 99.84 | 99.68 | 99.41 | 96.28 |
| % Highest Impurity | | 0.07 | 0.15 | 1.06 |
| Formulation E Bortezomib (1 mg/ml) in 90% PG and 10% Acetate Buffer with NAC | | | | |
| Assay % | 99.74 | 63 | 61 | 49.89 |
| % Highest Impurity | 0.16 | 26 | 20.47 | 31.7 |

Formulation B with PEG was not included in the study due to in solubility of the drug in PEG. As can be taken from the above results, stability of bortezomib is enhanced in the presence of PG, with % highest impurity of less than 1% when stored at accelerated storage conditions. Formulation with 10% of aqueous buffer also showed a comparable stability to that of formulation with PG alone. However increase in the buffer has revealed an undesirable increase in degradation products. Notably, the presence of a stabilizer/anti-oxidant like N-Acetyl Cysteine resulted in a significant degradation of the bortezomib.

Non-Aqueous Formulations (3):

Five substantially non-aqueous formulations were prepared with various ingredients as shown in Table 9. The formulations were prepared as follows: Degas the WFI to remove the dissolved oxygen in WFI and Propylene Glycol, refined Polyethylene Glycol 300 and acetate buffer, weigh required amount of bortezomib and add to the compounding vessel and dissolve in propylene glycol or polyethylene glycol in the compounding vessel with stirring. After complete dissolution of the drug add remaining amount of vehicle such propylene glycol, polyethylene glycol, and buffer. In case of the formulation with N-acetyl cysteine, ascorbic acid and sodium bisulphate, dissolve all these ingredients in acetate buffer under nitrogen and disperse it into the drug solution to make 1 mg/ml solutions.

TABLE 9

| Ingredients Conc. (mg/mL) | Batch Quantity A | Batch Quantity B | Batch Quantity C | Batch Quantity D | Batch Quantity E |
|---|---|---|---|---|---|
| Bortezomib | 25.0 mg | 25.0 mg | 25.0 mg | 25.0 mg | 25.0 mg |
| Propylene Glycol | 25 gm | 22.5 gm | 22.5 gm | 22.5 gm | 22.5 gm |
| Acetate Buffer | — | 2.5 gm | 2.5 gm | 2.5 gm | 2.5 gm |
| N-Acetyl Cysteine | — | — | 0.252 gm | — | — |
| Ascorbic Acid | — | — | — | 0.252 | — |
| Sodium Bisulphate | — | — | — | — | 0.125 gm |

Based on the above results, it is expected that batches A, B, D and E will provide the highest stability and that batch C will exhibit moderate degradation under corresponding storage conditions with respect to the results provided in Tables 6-8 above.

Several further compositions with substantially non-aqueous formulations were prepared with various ingredients and various examples listed in Table 10. In this example, the possible effects of super-refined solvents on the stability of bortezomib was investigated essentially as described above. Solutions were prepared as follows: Degas the WFI to remove the dissolved oxygen in WFI and Propylene Glycol, Refined PG, refined Polyethylene Glycol 300 (PEG) and Acetate buffer, weigh required amount of Bortezomib and add to the compounding vessel and dissolve in PG and PEG in the compounding vessel with stirring to make 2 mg/ml solution. The stock solution was further diluted to 1 mg/ml by adding remaining amount of vehicle such as PG, PEG and acetate buffer.

TABLE 10

Initial Potency of the Formulation With PEG and PG

| | Formulation with PG | | | Formulation withSuper Refined PG | | | Formulation with Super Refined PEG | | |
|---|---|---|---|---|---|---|---|---|---|
| | 2 mg/ml | 1 mg/ml | 1 mg/ml with 20% acetate Buffer | 2 mg/ml | 1 mg/ml | 1 mg/ml with 20% acetate Buffer | 2 mg/ml | 1 mg/ml | 1 mg/ml with 20% acetate Buffer |
| % Assay | 99.2 | 99.2 | 99.2 | 99.12 | 99.1 | 99.37 | 95.8 | 94.8 | 95.8 |
| % Highest Impurity | 0.8 | 0.8 | 0.91 | 0.88 | ND | 0.63 | 4.2 | 5.17 | 4.19 |

Remarkably, the results indicate that there is no influence of the type of PG used in the formulation. However, the inventors have observed a significant degradation of bortezomib in the presence of super-refined PEG. This indicates that bortezomib can be stabilized in presence of propylene glycol, but can not be stabilized in the presence of a closely related alternative glycolic solvent, PEG.

It should be apparent to those skilled in the art that many more modifications besides those already described are possible without departing from the inventive concepts herein. The inventive subject matter, therefore, is not to be restricted except in the scope of the appended claims. Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced. Where the specification claims refers to at least one of something selected from the group consisting of A, B, C . . . and N, the text should be interpreted as requiring only one element from the group, not A plus N, or B plus N, etc.

What is claimed is:

1. A ready to inject pharmaceutical parenteral composition, comprising:
    a liquid formulation comprising Bortezomib and an acidic buffer;
    wherein the liquid formulation is a substantially non-aqueous solvent system suitable for injection, and present in a container in a quantity suitable for at least two independent administrations;
    wherein the solvent system comprises at least 50 vol % propylene glycol;
    wherein the Bortezomib is present at a pharmaceutically effective concentration; and
    wherein the solvent system is formulated to maintain degradation of the Bortezomib at a level of less than 10 wt % when the liquid formulation is stored over at least three months at ambient conditions.

2. The ready to inject pharmaceutical parenteral composition in the multi-use container of claim 1 wherein the Bortezomib is present in an amount of at least 10 mg.

3. The ready to inject pharmaceutical parenteral composition in the multi-use container of claim 1 wherein the substantially non-aqueous solvent system comprises at least 90 vol % propylene glycol.

4. The ready to inject pharmaceutical parenteral composition in the multi-use container of claim 1 wherein the multi-use container comprises at least one of an ampoule, a vial, a pre-filled syringe, and an intravenous bag, and wherein the liquid formulation has not undergone lyophilization before being stored over the at least three months at ambient conditions.

5. The ready to inject pharmaceutical parenteral composition in the multi-use container of claim 1 wherein the substantially non-aqueous solvent system further comprises a polar solvent in an amount of equal to or less than 25 vol %.

6. The ready to inject pharmaceutical parenteral composition in the multi-use container of claim 5 wherein the substantially non-aqueous solvent system further comprises a polar solvent in an amount of equal to or less than 20 vol %.

7. The ready to inject pharmaceutical parenteral composition of claim 5 or claim 6 wherein the polar solvent is ethanol.

8. The ready to inject pharmaceutical parenteral composition in the multi-use container of claim 1 wherein the Bortezomib is present in an amount of at least 25 mg.

9. The ready to inject pharmaceutical parenteral composition in the multi-use container of claim 1 wherein the solvent system is formulated to maintain degradation of the Bortezomib at a level of less than 2 wt % when the liquid formulation is stored over at least three months at ambient conditions.

10. The ready to inject pharmaceutical composition in the multi-use container of claim 1, wherein the Bortezomib is present in an amount suitable to allow at least ten independent administrations.

11. A storage stable pharmaceutical parenteral composition comprising:
    a liquid formulation comprising Bortezomib and an acidic buffer;
    wherein the liquid formulation is a substantially non-aqueous solvent system for injection;
    wherein the solvent system comprises at least 50 vol % propylene glycol;

wherein the Bortezomib is present at a pharmaceutically effective concentration;

wherein the solvent system is formulated to maintain degradation of the Bortezomib at a level of less than 10 wt % when the liquid formulation is stored over at least three months at ambient conditions.

12. The storage stable pharmaceutical parenteral composition of claim 11 wherein the solvent system is formulated to maintain degradation of the Bortezomib at a level of less than 2 wt % when the liquid formulation is stored over at least three months at ambient conditions.

* * * * *